United States Patent
Sörner

(10) Patent No.: US 10,594,913 B2
(45) Date of Patent: Mar. 17, 2020

(54) HEAD/EYE TRACKING WITH LIGHT SOURCE PREHEATING

(71) Applicant: Smart Eye AB, Göteborg (SE)

(72) Inventor: Per Sörner, Göteborg (SE)

(73) Assignee: Smart Eye AB, Göteborg (SE)

( * ) Notice: Subject to any disclaimer, the term of this patent is extended or adjusted under 35 U.S.C. 154(b) by 0 days.

(21) Appl. No.: 16/335,491

(22) PCT Filed: Sep. 28, 2017

(86) PCT No.: PCT/EP2017/074664
§ 371 (c)(1),
(2) Date: Mar. 21, 2019

(87) PCT Pub. No.: WO2018/060350
PCT Pub. Date: Apr. 5, 2018

(65) Prior Publication Data
US 2019/0222731 A1    Jul. 18, 2019

(30) Foreign Application Priority Data
Sep. 30, 2016   (EP) ..................................... 16191827

(51) Int. Cl.
*H04N 5/225*    (2006.01)
*A61B 3/113*    (2006.01)
(Continued)

(52) U.S. Cl.
CPC ........... *H04N 5/2256* (2013.01); *A61B 3/113* (2013.01); *A61B 5/1114* (2013.01); *A61B 5/18* (2013.01);
(Continued)

(58) Field of Classification Search
CPC .............................. G02B 21/00; G06K 9/00597
(Continued)

(56) References Cited

U.S. PATENT DOCUMENTS

| 5,003,692 | A |   | 4/1991 | Izumi et al. |
| 5,016,282 | A | * | 5/1991 | Tomono ................. G06F 3/013 382/117 |

(Continued)

FOREIGN PATENT DOCUMENTS

| EP | 0883195 A1 | 12/1998 |
| JP | 2010258350 A | 11/2010 |

(Continued)

OTHER PUBLICATIONS

PCT International Search Report and Written Opinion for PCT Application No. PCT/2017/074664 filed Sep. 28, 2017 which is the parent application to the instant application; dated Dec. 20, 2017, 9 pages.

(Continued)

*Primary Examiner* — Thai Q Tran
*Assistant Examiner* — Syed Y Hasan
(74) *Attorney, Agent, or Firm* — Harness, Dickey & Pierce, P.L.C.; Anthony G. Fussner

(57) ABSTRACT

A head/eye tracking system comprising an image sensor for acquiring images of a user, a narrow band light source for illuminating the eyes, and a band-pass filter arranged between the eyes and the image acquisition device and having a pass-band corresponding to the emission spectrum of the light source at a predefined operating temperature. The system further comprises a heat source arranged in proximity to the light source and configured to preheat the light source to reach the predefined operating temperature. By shortening the period during which large temperature variation takes place, sub-optimal performance of the system can be accepted during this short period, thereby relaxing the requirements on light source and filter design.

14 Claims, 2 Drawing Sheets

(51) Int. Cl.
   *G02B 27/00* (2006.01)
   *A61B 5/11* (2006.01)
   *A61B 5/18* (2006.01)
   *G06F 3/01* (2006.01)
   *H05B 1/02* (2006.01)
   *G06K 9/00* (2006.01)
   *G02B 21/00* (2006.01)
   *G02B 5/28* (2006.01)

(52) U.S. Cl.
   CPC ......... *G02B 27/0093* (2013.01); *G06F 3/012* (2013.01); *G06F 3/013* (2013.01); *H05B 1/025* (2013.01); *G02B 5/28* (2013.01); *G02B 21/00* (2013.01); *G06K 9/00* (2013.01); *H05B 2203/02* (2013.01)

(58) Field of Classification Search
   USPC ............................................ 348/79; 382/117
   See application file for complete search history.

(56) References Cited

U.S. PATENT DOCUMENTS

2011/0304281 A1  12/2011  McEldowney et al.
2016/0117554 A1   4/2016  Kang et al.

FOREIGN PATENT DOCUMENTS

WO    WO-2013/072706 A1    5/2013
WO    WO-2015/034801 A2    3/2015

OTHER PUBLICATIONS

European Search Report for EP application No. 16191827 filed Sep. 30, 2016, dated Mar. 28 2017, 5 pages.

* cited by examiner

HEAD/EYE TRACKING WITH LIGHT SOURCE PREHEATING

This patent application is a U.S. national stage filing under 35 U.S.C. § 371 of PCT International Application No. PCT/EP2017/074664 filed Sep. 28, 2017 (published as WO2018/060350 on Apr. 5, 2018), which claims priority to and the benefit of European Application No. 16191827.1 filed Sep. 30, 2016. The entire contents of these applications are incorporated herein by reference in their entirety.

FIELD OF THE INVENTION

The present invention relates to the field of head or eye tracking, i.e. monitoring and tracking the head or eyes of a user by means of image acquisition and processing.

BACKGROUND OF THE INVENTION

Most head/eye tracking systems employ illumination of the object (i.e. the eyes of a user) in order to improve performance of the system. In order for such illumination to be distinguishable, the system should, as far as possible, be able to suppress ambient light.

In order to eliminate or minimize interference from ambient light, the illumination of a head/eye tracking system can be restricted to a narrow wavelength range, preferably outside the visible light spectrum. Typically, a light source having a light emission spectrum concentrated around a distinct center wavelength outside the visible spectrum is used in combination with a band-pass filter having a pass-band centered around the center wavelength.

The light source can be a solid state light source, such as a LED with a center wavelength in the near infra red (NIR) region, e.g. 840 nm or 940 nm. The filter has a pass-band enabling capturing of most light emitted by the light source, while at the same time blocking most ambient light. As an example, the pass-band of the filter is ±25 nm.

One particular challenge is sunlight, which has a relatively high irradiance (flux per area) over a broad spectrum, including NIR. In particular some automotive applications present challenges with strong sunlight.

In the NIR region, the spectral irradiance (flux per area per wavelength) of sunlight is approximately 1 $W/m^2/nm$, so that the total irradiance of sunlight admitted by the filter mentioned above is around 50 $W/m^2$. In order to distinguish illumination from the light source from sunlight, the irradiance of the light source (flux per area) thus needs to be in the same order of magnitude (50 $W/m^2$). The required electrical power can be limited by using pulsed light, and in a typical implementation the light source has an electrical power as low as 1-2 W.

One issue in this context is that light sources such as LEDs have a temperature drift, i.e. the center wavelength will shift slightly when the temperature changes. As an example, for a typical LED the temperature drift is a few tenth nm/K. The pass-band of the filter therefore needs to be chosen to correspond to the LED emission spectrum in the expected operating temperature. For many applications, e.g. indoor applications without significant temperature variations, this will not present any significant problem. However, in some applications, such as automotive applications, there will be significant variations in the operating temperature of the LED.

In a typical automotive installation, the LED temperature may change from an initial temperature, which may be as low as minus 30 degrees Celsius or less, up to a steady-state operating temperature of the LED circuitry. Depending on the ambient temperature and installation-specific thermal resistance, this steady-state operating temperature may be as low as 20 degrees Celsius and as high as 90 degrees Celsius. This corresponds to a shift of the LED center wavelength of around 30-40 nm, i.e. in the same order of magnitude as the pass-band of the filter. In worst case, most of the emitted light will be lost. If also the initial phase is accounted for, i.e. the time period before the LED reaches the steady state operating temperature, the active operating temperature range becomes even greater.

In order to compensate for this temperature drift, and ensure satisfactory system performance also in a worst-case scenario, the pass-band of the filter may be wider, so as to ensure that most of the power emitted by the LED will pass the filter at all expected temperatures. However, as a consequence, the filter will also allow more sunlight to pass, and therefore the power of the LED needs to be increased, typically by a factor of two or three.

GENERAL DISCLOSURE OF THE INVENTION

It is an object of the present invention to enable the illumination of a head/eye tracking system to suppress ambient light (in particular sunlight) also under conditions of large temperature variations, without requiring increased power.

This and other objects are achieved by a head/eye tracking system comprising an image sensor for acquiring images of a user, a narrow band light source for illuminating the user, and a band-pass filter arranged between the user and the image acquisition device and having a pass-band corresponding to the emission spectrum of the light source at a predefined operating temperature. The system further comprises a heat source arranged in proximity to the light source and configured to preheat the light source to reach a temperature range including the predefined operating temperature.

The invention is based on the realization that the variation in steady-state operating temperature can be reduced by preheating the light source to (or close to) a predefined operating temperature using a heat source. By means of the preheating, lower steady-state temperatures, which could result from low ambient temperatures, can be avoided. This means that the operating temperature becomes more predictable.

As an example, the temperature range can be +/−15 degrees or smaller. The important thing is that the variation of the steady-state operating temperature of the light source will be significantly smaller than for a system without preheating.

Another advantage with the preheating according to the invention is that the start-up phase, i.e. the time from start-up until the light source reaches its steady-state operating temperature, may be significantly shortened. Without preheating, this period may be several minutes, and during this period the matching of the filter and light source may be relatively poor. With preheating according to the invention, the start-up period can be as short as 30 seconds or less.

The predefined operating temperature can be selected to be in the upper range of expected operating temperatures. As an example, the predefined operating temperature is more than 75 degrees Celsius, preferably more than 80 degrees Celsius. It is noted that it may be possible that extreme conditions result in an operating temperature above the predefined operating temperature. However, even for such unlikely operating conditions, the resulting operating temperature will not be significantly higher than the predefined operating temperature for which the filter is configured.

It is noted that the preheating does not need to be very accurately controlled. As long as the operating temperature is within a given range of the specified operating temperature, such as ±15 degrees, the temperature drift of the light source will not cause significant problems.

In some embodiments, the predefined operation temperature is a function of parameters of the light source and/or the filter, so that the system performance is optimized with respect to the individual components used.

In a simple implementation, the heat source can be self-regulating, e.g. a PTC thermistor. Alternatively, the heat source is provided with active temperature feedback control.

The expression "narrow band" light source is intended a light source having a light emission spectrum concentrated within 100 nm, or preferably within 50 nm. The light emission spectrum of the light source is further preferably outside the visible spectrum.

BRIEF DESCRIPTION OF THE DRAWINGS

The present invention will be described in more detail with reference to the appended drawings, showing currently preferred embodiments of the invention.

DETAILED DESCRIPTION OF PREFERRED EMBODIMENTS

Embodiment of the present invention will now be discussed with reference to an eye tracking system. However, the principles of the invention are equally applicable to a head tracking system, or indeed any application where a band-pass filtered image acquisition needs to be matched to a light source emission spectrum.

Figure 1:
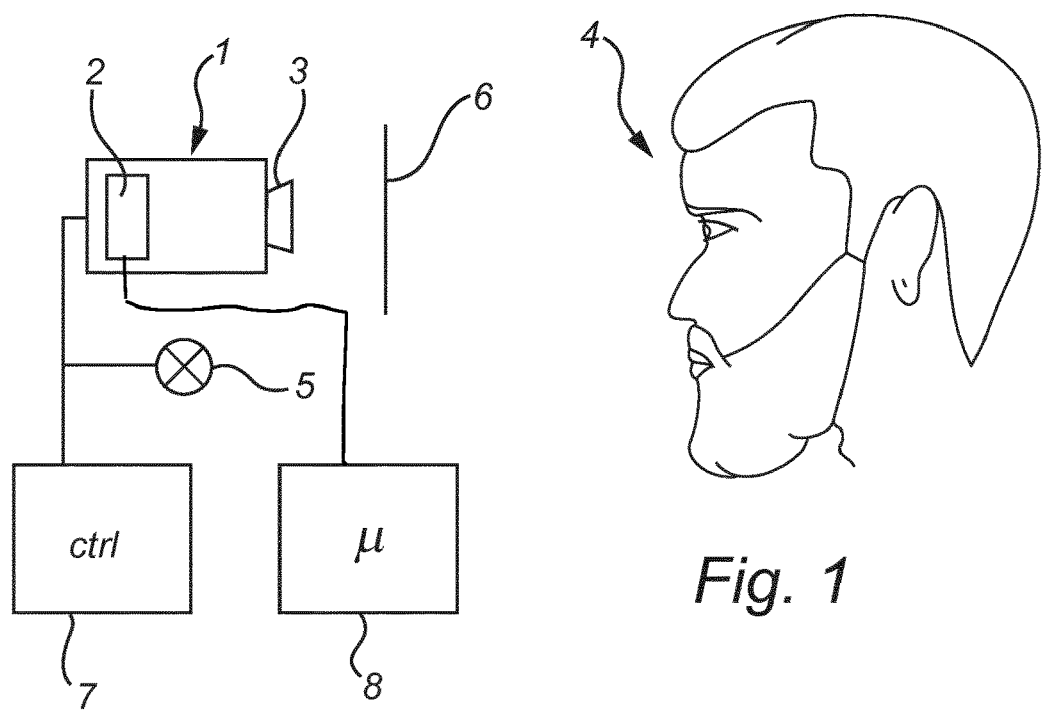
FIG. 1 shows a schematic view of an eye tracking system in which the present invention may be applied.

The eye tracking system in FIG. 1 includes an image acquisition device, or camera 1, including an image sensor 2, e.g. a CMOS image sensor, and suitable optics 3. The camera 1 is arranged to acquire images of a user 4, more specifically the eyes of the user. The system further comprises a light source 5, typically configured to emit light outside the visible range such as infra red (IR) or near infra red (NIR). The light source may be a solid state light source, such as a LED. In the illustrated example, the light source 5 is a LED configured to emit light with a light spectrum concentrated in a 50 nm band centered around 850 or 940 nm (NIR). Further, an optical band-pass filter 6, e.g. an interference filter, is arranged between the user and the camera 1. The filter 6 is configured to have a pass-band substantially corresponding to the light emission spectrum of the light source 5. So, in the above mentioned example, the filter 6 should have a pass-band of around 825-875 nm, or 915-965 nm.

A controller 7 is connected to the camera 1 and LED 5, and programmed to control the sensor 2 to acquire consecutive images under illumination by the LED 5. Typically, the LED 5 is driven with a given duty cycle, and the controller 7 then controls the sensor 1 to acquire images in synchronization with the light pulses from the LED 5.

The system further comprises processing circuitry 8 connected to receive images acquired by the sensor 2. The processing circuitry is further programmed to track movement in the eyes, in order to acquire various information. For example, the processing circuitry may be programmed to obtain the direction of gaze of the user, or to detect drowsiness of the user.

The system in FIG. 1 has many different applications, including automotive applications where the eyes of a driver are tracked e.g. for safety reasons. In such applications, the user 4 may be exposed to strong ambient light from the sun, sometimes direct sunlight.

During operation, the user 4 is illuminated by the light source, and light reflected from the object passes the filter and is received by the camera optics 3 and stored in the sensor 2. It is noted that most ambient light, including all visible light, will be blocked by the filter. However, in a situation where the spectrum of ambient light includes the pass-band of the filter 6, such light will also be received by the camera 1. As mentioned above, sunlight does include such wavelengths, and typically has a spectral irradiance (flux per area per wavelength) of about 1 W/m$^2$/nm in the relevant wavelength range. The power of the light source is therefore configured to provide sufficient spectral power to be distinguishable from sunlight. As an example, the LED 5 has an electrical power of 1-2 W.

Figure 2:
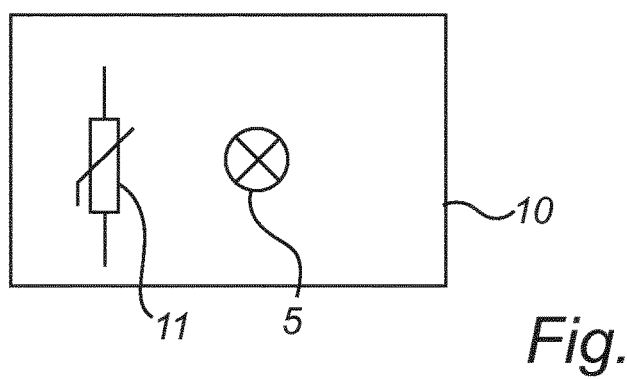
FIG. 2 shows a schematic block diagram of a first embodiment of the present invention.
Figure 3:
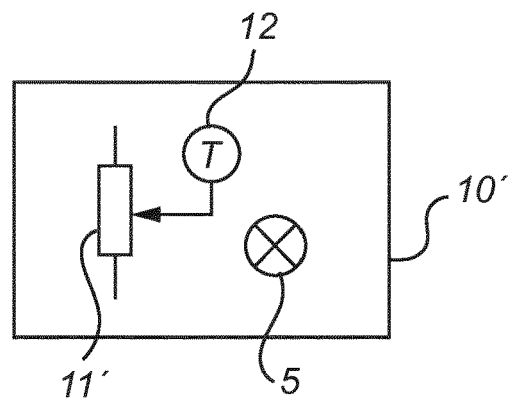
FIG. 3 shows a schematic block diagram of a second embodiment of the present invention.

In accordance with the present invention, and with reference to FIG. 2-3, the LED 5 forms part of a lighting device 10, 10', further including a heat source 11, 11'. The heat source is arranged in thermal contact with the LED 5, either in direct contact or by mounting on a common circuit board, in order to enable preheating of the LED 5. The purpose of the preheating is to quickly heat the LED to a predefined operating temperature, or at least within a given range (e.g. +/−15 degrees) of that predefined operating temperature. This avoids a large variation in the steady-state operating temperature of the LED, thus enabling a better matching of the filter pass band. Also, the start-up time, i.e. the time when the LED is heated from an initial temperature to the steady-state temperature can be shortened. As an example, the start-up period can be shortened from several minutes to less than 30 seconds, or even less than 15 seconds.

With reference to FIG. 2, the heat source 11 is a self-regulating heat source, i.e. a positive temperature thermistor. A PTC thermistor will exhibit an increasing resistance with temperature, such that its temperature will stabilize at a given ambient temperature when connected to a given voltage. In this case, there is no actual feedback from the LED 5 itself, but the resulting heating of the LED 5 will be determined by the ambient temperature surrounding the PTC 13, the thermal exchange between the LED and the ambient, and of course the heating of the LED caused by its operation. By an appropriate selection of self-regulating heat source 11 and mounting of the heat source 11 and LED 5, a desired preheating of the LED 5 can be achieved.

Alternatively, as shown in FIG. 3, the lighting device 10' further comprises active control circuitry 12, configured to detect the temperature of the LED 5, and to apply feedback control of the heat source 11' in order to heat the LED 5 until it reaches a predefined temperature.

Figure 4:
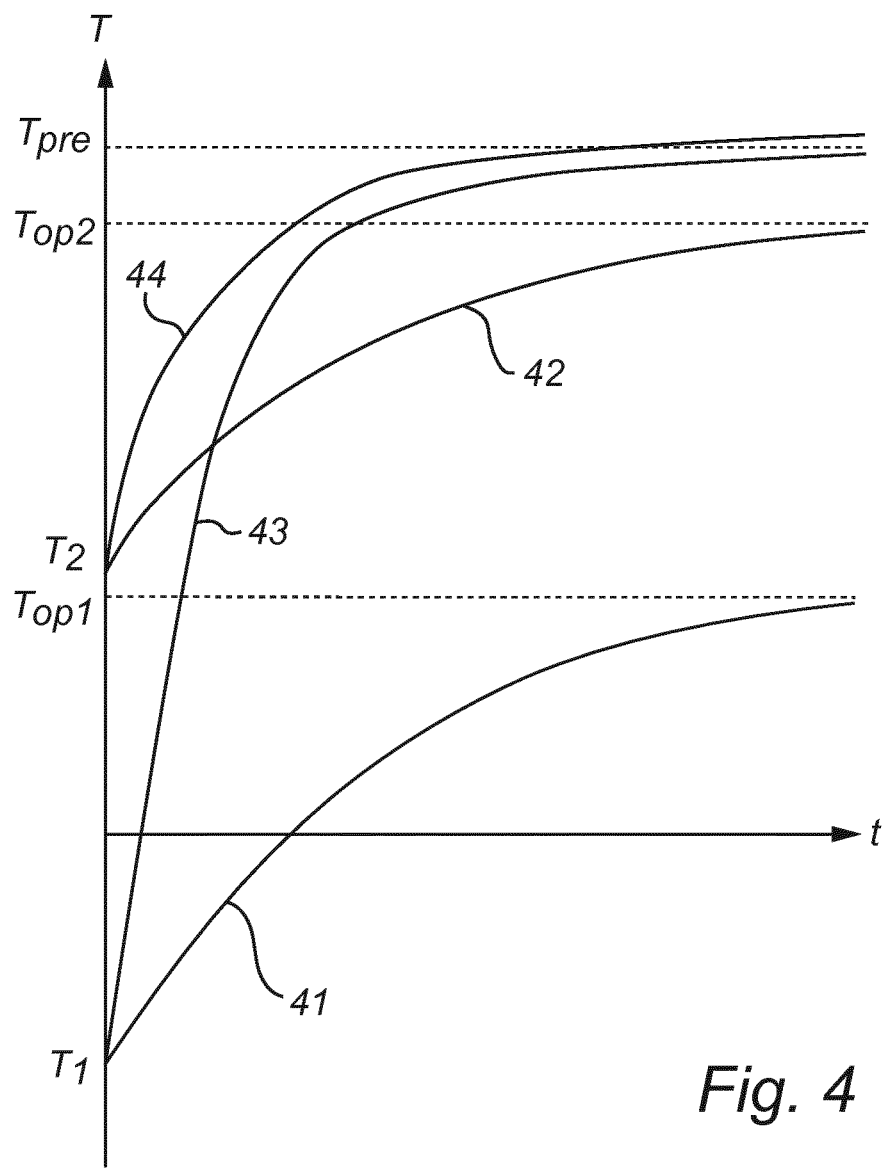
FIG. 4 is a diagram showing temperature of a LED over time.

FIG. 4 illustrates a possible outcome of preheating according to the present invention expressed as a diagram showing temperature over time.

In a conventional system, the light source will typically be gradually heated from an initial temperature up to a steady-state operating temperature. The initial temperature will depend primarily on the ambient temperature, which, in the case of an automobile, can be very low, potentially as low as minus 30 degrees Celsius or lower. The steady-state operating temperature will also depend on the ambient temperature, but also on the power of the LED, heat exchange between the LED and the mechanical mounting structure (e.g. the presence of any heat sinks such as heat fins), as well as the amount of heat dissipation (e.g. air transport of heat). As an example, in a typical installation, the steady-state operating temperature of the LED may be up to 50 degrees higher than the ambient temperature. The time period required to reach the steady-state operating temperature will of course also depend on various factors, but is typically in the order of minutes.

In FIG. 4, curves 41 and 42 indicate the temperature of a LED in a conventional eye tracking system for two different ambient temperatures $T_0$ and $T_1$. As discussed above, the curve exhibits two separate phases. In a first, initial phase, the temperature gradually increases from the initial temperature $T_1$, $T_2$ to a steady-state operating temperature range $T_{op1}$, $T_{op2}$. During a second phase, the temperature remains within this range. As indicated in FIG. 4, the steady-state operating temperature range will be lower for a lower initial temperature.

Curves 43 and 44 indicate the temperature of a LED provided with preheating according to en embodiment of the present invention, again for the two different ambient temperatures $T_1$ and $T_2$. In this case, the preheating causes the LED to approach the predefined operating temperature $T_{pre}$ within a relatively short time period. It is noted that the difference in ambient temperature (as well as possibly other factors) may result in a slight difference in steady state operating temperature in the two curves 43 and 44. In the example in FIG. 4, this steady state operating temperature for curve 44 is slightly higher than for curve 43.

FIG. 4 clearly illustrates the two main advantages of the present invention. To begin with, the preheating ensures that the steady state operating temperature for both ambient temperatures $T_1$ and $T_2$ is equal to (or close to) the predefined operating temperature $T_{pre}$. The pass band of the filter can thus be chosen to correspond to the light emission spectrum at this temperature. Further, the preheating reduces the initial phase, i.e. the time during which the LED temperature rises from the initial temperature to the steady-state operating temperature. This ensures that any period during which the filter is not matched with the emitted light spectrum will be minimized.

The person skilled in the art realizes that the present invention by no means is limited to the preferred embodiments described above. On the contrary, many modifications and variations are possible within the scope of the appended claims. For example, the eye tracking system may comprise more than one light source, e.g. for purposes of glare or reflex reduction. Further, different solutions may be chosen to implement the heat source, without departing from the present invention as defined by the claims.

The invention claimed is:

1. An head/eye tracking system comprising:
   an image sensor for acquiring images of a user;
   a narrow band light source for illuminating the user; and
   a band-pass filter arranged between the user and the image acquisition device and having a pass-band corresponding to the emission spectrum of the narrow band light source for a predefined operating temperature; and
   a heat source arranged in proximity to the narrow band light source and configured to preheat the narrow band light source to a temperature range including the predefined operating temperature.

2. The head/eye tracking system of claim 1, wherein the heat source is self-regulating.

3. The head/eye tracking system of claim 2, wherein the heat source is a PTC thermistor.

4. The head/eye tracking system of claim 1, wherein the heat source is provided with active temperature feedback control.

5. The head/eye tracking system of claim 1, wherein the heat source is configured such that the narrow band light source reaches the predefined operating temperature in less than 30 seconds.

6. The head/eye tracking system of claim 1, wherein the predefined operating temperature is above 70 degrees Celsius, preferably above 80 degrees Celsius.

7. The head/eye tracking system of claim 1, wherein the narrow band light source has a light emission spectrum concentrated within 100 nanometers, preferably within 50 nanometers.

8. The head/eye tracking system of claim 1, wherein the narrow band light source has a light emission spectrum outside the visible spectrum.

9. The head/eye tracking system of claim 1, wherein the temperature range is +/−15 degrees of the predefined operating temperature.

10. The head/eye tracking system of claim 1, wherein the predefined operation temperature is a function of parameters of the narrow band light source and/or the band-pass filter.

11. A method for head/eye tracking comprising:
    illuminating a user using a narrow band light source;
    acquiring band-pass filtered images of the user, where a pass-band of the filtering corresponds to the emission spectrum of the narrow band light source for a predefined operating temperature; and
    preheating the narrow band light source to a temperature range including the predefined operating temperature using a heat source arranged in proximity to the narrow band light source.

12. The method of claim 11, wherein the temperature range is +/−15 degrees of the predefined operating temperature.

13. The method of claim 11, wherein the heat source is configured such that the light source reaches the predefined operating temperature in less than 30 seconds.

14. The method of claim 11, wherein the predefined operating temperature is above 70 degrees Celsius, preferably above 80 degrees Celsius.

* * * * *